(12) United States Patent
Singhal

(10) Patent No.: US 10,300,258 B2
(45) Date of Patent: May 28, 2019

(54) APPARATUS AND METHOD FOR NATURAL CURE OF MIDDLE EAR INFECTIONS WITHOUT ANTIBIOTICS

(71) Applicant: Tara Chand Singhal, Torrance, CA (US)

(72) Inventor: Tara Chand Singhal, Torrance, CA (US)

(*) Notice: Subject to any disclaimer, the term of this patent is extended or adjusted under 35 U.S.C. 154(b) by 1110 days.

(21) Appl. No.: 13/850,167

(22) Filed: Mar. 25, 2013

(65) Prior Publication Data

US 2014/0288532 A1  Sep. 25, 2014
US 2016/0213903 A9  Jul. 28, 2016

Related U.S. Application Data

(60) Provisional application No. 61/719,961, filed on Oct. 30, 2012.

(51) Int. Cl.
*A61K 36/31* (2006.01)
*A61M 31/00* (2006.01)
*C11B 9/00* (2006.01)

(52) U.S. Cl.
CPC ............ *A61M 31/00* (2013.01); *A61K 36/31* (2013.01); *A61M 2205/3368* (2013.01); *A61M 2210/0662* (2013.01); *A61M 2210/0668* (2013.01); *C11B 9/00* (2013.01)

(58) Field of Classification Search
CPC .......... A61M 31/00; A61M 2205/3368; A61M 2210/0662; A61M 2210/0668; A61K 36/31; C11B 9/00

USPC ................. 604/212, 216, 514–517
See application file for complete search history.

(56) References Cited

U.S. PATENT DOCUMENTS

| | | | |
|---|---|---|---|
| 79,742 A * | 7/1868 | Faloon | A61M 3/0262 604/212 |
| 6,257,759 B1 * | 7/2001 | Witonsky | G01K 11/165 116/207 |
| 8,177,740 B1 * | 5/2012 | McGlothlin | A61M 5/152 604/82 |
| 8,425,474 B2 * | 4/2013 | Glassman | A61M 31/00 206/528 |
| 2005/0224082 A1 * | 10/2005 | Johnson | A61F 11/08 128/864 |

(Continued)

OTHER PUBLICATIONS

"Otitis Media." University of Maryland Medical Center. Last Reviewed Feb. 3, 2016. http://www.umm.edu/health/medical/altmed/condition/otitis-media. Accessed Dec. 20, 2017.*

(Continued)

*Primary Examiner* — Bhisma Mehta
*Assistant Examiner* — Larry R. Wilson
(74) *Attorney, Agent, or Firm* — Steve Roeder, Esq.

(57) ABSTRACT

An apparatus for natural treatment for middle ear infection has a single use sachet. The sachet has a pocket that holds a limited quantity of mustard essential oil. The sachet has a neck and a dropper and the sachet can be squeezed to flow drops for pouring into an ear canal. The sachet is put in a microwave oven just before use for only substantially 30 seconds to heat the oil and up to five drops of heated oil is squeezed into an ear canal of a person with severe ear itching indicative of a middle ear infection.

16 Claims, 5 Drawing Sheets

(56) References Cited

U.S. PATENT DOCUMENTS

| | | | | |
|---|---|---|---|---|
| 2005/0256082 | A1* | 11/2005 | Nonomura | A61K 8/0229 |
| | | | | 514/57 |
| 2006/0253087 | A1* | 11/2006 | Vlodaver | A61F 11/00 |
| | | | | 604/275 |
| 2010/0172941 | A1* | 7/2010 | Vajdy | A61K 39/145 |
| | | | | 424/283.1 |

OTHER PUBLICATIONS

Kumari, Kalpana. "Earache Remedies for Children". Published: Oct. 12, 2009. http://www.buzzle.com/articles/earache-remedies-for-children.html. Accessed Apr. 28, 2016.*

Natural Healing Guide. "Home Remedies, Remedies for Ears—Remedy (Nuskhe)". Published Dec. 14, 2011. https://web.archive.org/web/20111214181811/http://natural-healing-guide.com/Home-Remedies/Ear-Ache.htm. Accessed Apr. 26, 2018.*

("Reservoir" Dictionary.com Unabridged. https://www.dictionary.com/browse/reservoir. Accessed Dec. 14, 2018 (Year: 2018).*

* cited by examiner

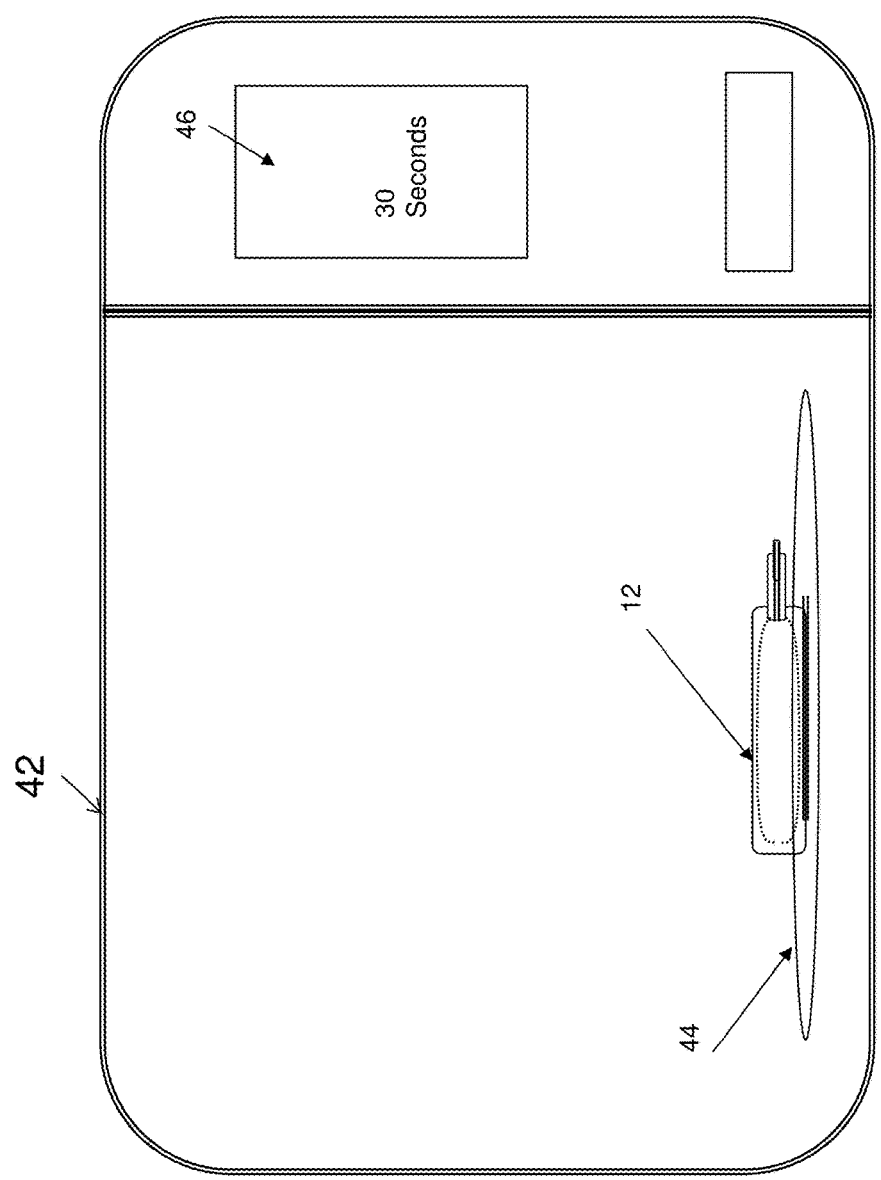

APPARATUS AND METHOD FOR NATURAL CURE OF MIDDLE EAR INFECTIONS WITHOUT ANTIBIOTICS

CROSS REFERENCE

This application claims priority from Provisional application Ser. No. 61/719,961, filed on Oct. 30, 2012 of Tara Chand Singhal, for Apparatus and Method for Natural Cure of Middle Ear Infections Without Antibiotics. The contents of application Ser. No. 61/719,961 are incorporated herein by reference.

FIELD OF THE INVENTION

An apparatus for natural cure for middle ear infection that uses a single use sachet with a pocket that holds a limited quantity of mustard essential oil is described. The sachet has a neck and a dropper and sachet can be squeezed to flow drops for pouring into an ear canal.

BACKGROUND

Next to the common cold, ear infections are the most commonly diagnosed childhood illness in the United States. More than 3 out of 4 kids have had at least one ear infection by the time they reach 3 years of age. Adults are not immune from ear infections even though they get it much less frequently.

To understand how ear infections develop, let's review how the ear works. Every time one hears a sound, the various structures of the ear have to work together to make sure the information gets to the brain.

The ear is responsible for hearing and balance and is made up of three parts—the outer ear, middle ear, and inner ear. Hearing begins when sound waves that travel through the air reach the outer ear, or pinna, which is the part of the ear that's visible. The sound waves then travel from the pinna through the ear canal to the middle ear, which includes the eardrum (a thin layer of tissue) and three tiny bones called ossicles. When the eardrum vibrates, the ossicles amplify these vibrations and carry them to the inner ear.

The inner ear translates the vibrations into electric signals and sends them to the auditory nerve, which connects to the brain. When these nerve impulses reach the brain, they're interpreted as sound. To function properly, the middle ear must be at the same pressure as the outside world. This is taken care of by the Eustachian tube, a small passage that connects the middle ear to the back of the throat behind the nose.

By letting air reach the middle ear, the Eustachian tube equalizes the air pressure in the middle ear to the outside air pressure. (When your ears "pop" while yawning or swallowing, the Eustachian tubes are adjusting the air pressure in your middle ears.) The Eustachian tube also allows for drainage of mucus from the middle ear into the throat. Sometimes, the Eustachian tube may malfunction. For example, when someone has a cold or an allergy affecting the nasal passages, the Eustachian tube may become blocked by congestion in its lining or by mucus within the tube. This blockage will allow fluid to build up within the normally air-filled middle ear.

Bacteria or viruses that have entered the middle ear through the Eustachian tube also can get trapped in this way. These germs can breed in the trapped fluid, eventually leading to an ear infection.

An ear infection (acute otitis media) is most often a bacterial or viral infection that affects the middle ear, the air-filled space behind the eardrum that contains the tiny vibrating bones of the ear. Children are more likely than adults to get ear infections.

Ear infections are often painful because of inflammation and buildup of fluids in the middle ear. The onset of signs and symptoms of ear infection is usually rapid. Signs and symptoms of an ear infection can indicate a number of different conditions.

An ear infection is caused by a bacterium or virus in the middle ear. This infection often results from another illness—cold, flu or allergy—that causes congestion and swelling of the nasal passages, throat and Eustachian tubes.

The Eustachian tubes are a pair of narrow tubes than run from each middle ear to high in the back of the throat, behind the nasal passages. Swelling, inflammation and mucus in the Eustachian tubes from an upper respiratory infection or allergy can block them, causing the accumulation of fluids in the middle ear. A bacterial or viral infection of this fluid is usually what produces the symptoms of an ear infection.

Ear infections are more common in children, in part, because their Eustachian tubes are narrower and more horizontal—factors that make them more difficult to drain and more likely to get clogged.

Middle ear infection is common among people of all ages. The infection may arise due to many causes such as infection of the throat, and whenever the bacterium makes its way inside the ear canal.

The middle ear infection is quite painful and requires a visit to a doctor in an urgent care situation. The middle part of the ear is unreachable by the patient and cannot be treated by external use of ointments.

The doctor after examination of the ear canal and seeing redness associated with infection usually prescribes an antibiotic. The antibiotic treatment is usually taken for a set number of days, for example seven days, to get rid of the infection.

Based on medical science history, bacteria is known to develop resistance to antibiotics and hence for this reason the medical profession would rather not over prescribe antibiotics for conditions that can be cured otherwise. Unfortunately, western medical science has no alternative cure for middle ear infection.

Black and white mustards are used for culinary and medicinal purposes. The leaves, flowers, seeds, and oils of the black mustard are used, while only the seeds of the white mustard are useful. Black mustard powder is an important herbal remedy because it draws blood to the surface of the skin quickly, which means that it is rubefacient, and is warming. Mustard essential oil is used as an ingredient in liniments, stomach stimulants, and emetics.

Mustard is rich in many vitamins and nutrients that are beneficial to everyone. Mustard is rich in calcium and iron and helps to restore bacterial balance in the intestines. The mustard's greens are rich in vitamin A, iron, and zinc, and are best when eaten raw or steamed. White mustard has been used throughout the world to relieve pain, and as a diuretic and an antibiotic. Mustard flour is an antiseptic and can also be used as a deodorizer. The mustard's oil can be used for pain relief of arthritic conditions and chilblains. Mustard is also an excellent expectorant and a very powerful natural emetic.

Some of the most valuable properties of mustard lie in its warming and rubefacient properties. Black mustard and white mustard can be used to draw infection or congestion away from its source for nasal congestion, or for relief of an abscess. The rubefacient qualities help respiratory and circulatory disorders, including some heart problems.

It is the objective of the embodiments herein to have a cure for middle ear infection that does not require use of an antibiotic. It is further the objective to treat the infection without a visit to the doctor and much sooner than seven days. It is yet another objective to cure the middle ear infection at much lower cost than the combination of doctor fees and cost of antibiotics.

SUMMARY

Middle ear infections can be quickly ameliorated with use of mustard essential oil. The embodiments described here are an apparatus and a method for a single application for a natural cure for middle ear infection using mustard essential oil.

Essential oil is extracted by steam distillation of mustard seeds soaked in water. Alternatively for this application cold-pressed oil of mustard seeds may also be used.

Mustard essential oil has bactericidal or anti bacterial properties. Internally it fights bacterial infections in the colon, digestive system, excretory system, urinary tract etc. Externally applied, it can treat bacterial infections on skin. For tutorial purposes, the Background section provides an extract from Internet that describes various properties of mustard oil or essential oil.

As described in the embodiments herein, the middle ear infections can be quickly ameliorated with use of mustard essential oil. The embodiments describe here an apparatus for natural cure for middle ear infection. The apparatus has a single use sachet. The sachet has a pocket and the pocket holds a limited quantity of mustard essential oil. The sachet has a neck and a dropper and sachet can be squeezed to flow drops for pouring into an ear canal.

The mustard essential oil preferably is heated to about 115 degrees Fahrenheit. Therefore, the sachet is put in a microwave oven just before use for only substantially 30 seconds to heat the oil and up to five drops of heated oil is squeezed into an ear canal of a person with severe ear itching indicative of a middle ear infection.

The head is positioned on a side to have one ear facing up before dropping the oil in the ear canal and the head is stayed in position for substantially five minutes to have the oil flow deep in to the middle ear. The single use sachet is in a packaging with two cotton ear plugs.

The ear is plugged with the cotton plug and head is turned on the other side for dropping the oil into the other ear. This method of treatment of middle ear infection usually provides an instant relief from the itching and usually cures the infection in a single treatment as above. These and other aspects of the embodiments are described in detail here with the help of the accompanying figures.

BRIEF DESCRIPTION OF THE DRAWINGS

Some of the novel features of this invention will be best understood from the accompanying drawings, taken in conjunction with the accompanying description, in which similar reference characters refer to similar parts, and in which:

FIG. 3A is a block diagram that illustrates features of the present invention of a method of heating the oil in the sachet for middle ear infection cure;

DESCRIPTION

The embodiments described herein are directed to a natural cure for middle ear infection. The natural cure uses mustard essential oil and avoids use of antibiotics.

Figure 1B:
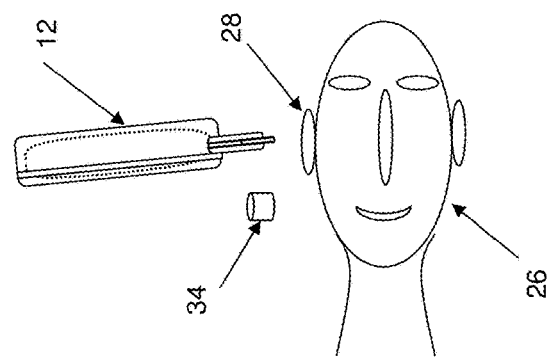
FIG. 1B is a block diagram that illustrates features of the present invention of using a sachet for cure of middle ear infection.
Figure 1A:
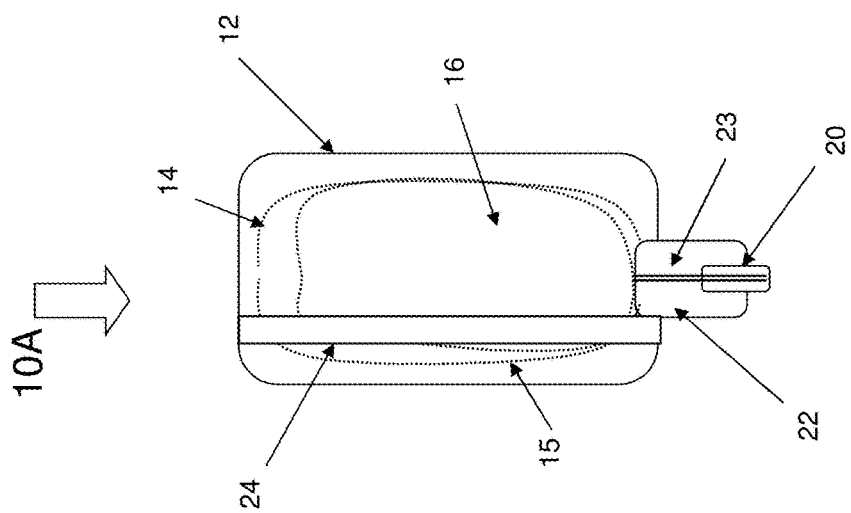
FIG. 1A is a block diagram that illustrates features of the present invention of a sachet for cure of middle ear infection.

With reference to FIG. 1A, an apparatus 10A for natural cure for middle ear infection is single use sachet 12. The sachet 12 holds limited quantity of mustard essential oil 16 inside a foil lined pocket 15. The foil lined pocket 15 is a squeezable pocket 14 to be able to squeeze drops of oil via the dropper 20 attached to neck 22.

FIG. 1B illustrates use of sachet 12 with a human head 26 positioned on the side exposing one of the human ear 28. An ear plug 34 is used after the oil had been put in the ear 28.

As illustrated in FIG. 1A, the sachet 12 has a pouch 14 and the pouch is sized to and holds a limited quantity of mustard essential oil 16. The quantity of mustard essential oil is limited to notionally ten drops and could be little more to account for the fact that not all oil in the sachet may be useable. The sachet 12 has a neck 22 and a dropper 20. The sachet 12 can be squeezed to flow drops of mustard essential oil for dropping into an ear canal via the dropper 20. The neck 22 provides a length that is suitable to be able to easily access the outer ear canal.

Similar sachets are used in prior art for application such as for dispensing beauty products, creams and medicinal ointments etc to the palm of the hand and/or fingers. Hence the technology of making such sachets is considered prior art.

Figure 2B:
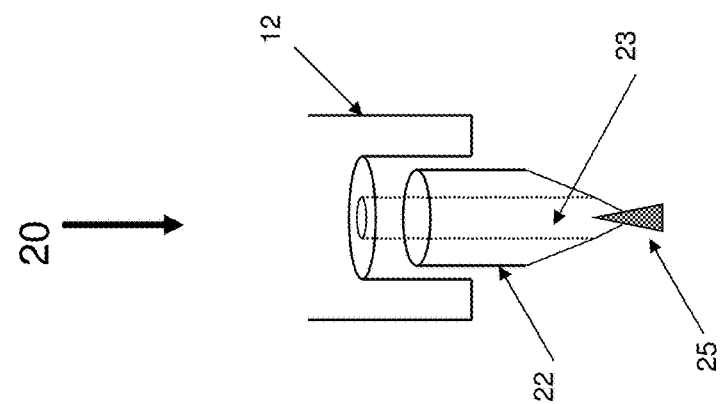
FIG. 2B is a block diagram that illustrates features of the present invention of dropper of a sachet for cure of middle ear infection.
Figure 2A:
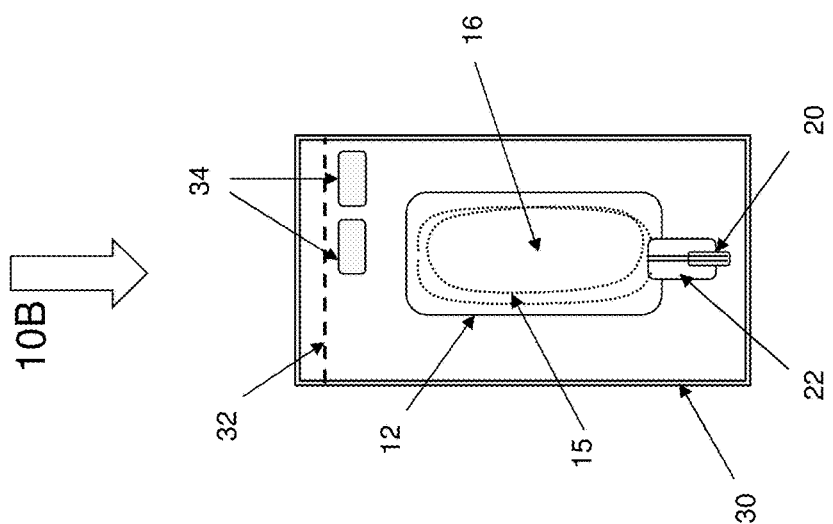
FIG. 2A is a block diagram that illustrates features of the present invention of packaging of a sachet for cure of middle ear infection.

As illustrated in FIG. 2A, in embodiment 10 ft the sachet 12 is packaged inside a package 30 and the package 30 has a tear open side 32 to be able to tear open package 30.

As illustrated later, with the help of FIGS. 3A and 3B, the sachet 12 and thus the oil 16 inside the sachet is heated to a comfortable therapeutic temperature of around 110 to 115 Fahrenheit degrees.

As illustrated in FIG. 1A, optionally the sachet 12 has attached a liquid crystal thermometer strip 24 which provides for an advisory that the oil is at a suitable temperature before the sachet should be used. The science of liquid crystal thermometer is prior art. A liquid crystal thermometer or plastic strip thermometer is a type of thermometer that contains heat-sensitive liquid crystals in a plastic strip that change color to indicate different temperatures.

Liquid crystals possess the mechanical properties of a liquid, but have the optical properties of a single crystal. Temperature changes can affect the color of a liquid crystal, which makes them useful for temperature measurement. The resolution of liquid crystal sensors is in the 0.1° C. range. Disposable liquid crystal thermometers have been developed for home and medical use. For example if the thermometer is black and it is put onto someone's forehead it will change color depending on the temperature of the person.

Liquid crystal thermometers portray temperatures as colors and can be used to follow temperature changes caused by heat flow. In medical applications, liquid crystal thermometers may be used to read body temperature by placing against the forehead.

In the application of the embodiments herein, the thermometer strip 24 is used to indicate to a user, as a precautionary measure, that the oil 16 is not hotter than in the range of 110 to 115 Fahrenheit degrees at the time of dropping the oil in the ear canal. This may be accomplished in other ways as well as such as by hand feel. The oil when heated may be above 115 Fahrenheit degrees as that temperature would drop before use.

As shown in FIG. 2A, the single use sachet 12 has in the packaging 30, two cotton ear plugs 34. These ear plugs 34 are intended to be used to plug the ear canal to prevent the oil that may flow out from the ear canal.

Alternatively, the sachet 12 may be in the form of a bottle (not shown) and different such embodiments are not ruled out. However, the sachet 12 is preferred, as given small quantity of mustard essential oil, a sachet given its size may be more convenient to handle and use. The sachet 12 may be one inch wide and two inches high. It is believed that such a size of sachet 12 would be convenient to hold and use for its intended purpose.

The ear plugs 34 are preferably cotton to absorb the oil that may leak out of the ear canal. However, other absorbent materials are not ruled out.

With reference to FIG. 2B, a close up of the construction of the dropper 20 is illustrated. The sachet 12 is integrally attached to a neck 22. The neck 22 has a channel 23 for squeezing the oil from the pocket 14 via the channel 23 to the ear canal when the pocket 14 with oil 16 is squeezed. A stopper 25 is attached to the end of the channel 23 and is removed or broken away before use.

A label informing a user about the contents and purpose of the package as well as an FDA advisory is provided on the package 30.

Instructions for the use of the sachet 12 are illustrated. The use instructions provide:

1. Open package and heat the sachet in microwave for only 30 seconds.
2. Put head on one side on pillow
3. Squeeze 2-4 drops in one ear, wait a few minutes and use supplied cotton ear plug.
4. Repeat steps 2 and 3 for the other ear.
5. Discard sachet after use.

Note: If symptoms of ear pain reappear, use a second sachet.

If problem does not disappear, consult a doctor

The sachet 12 is made of a material that can be put inside a microwave oven and heat the oil in the pouch. As illustrated with the help of FIG. 3A, if the sachet 12 is made of plastic, the sachet can be directly placed on the tray 44 of a microwave oven 42.

Figure 3B:
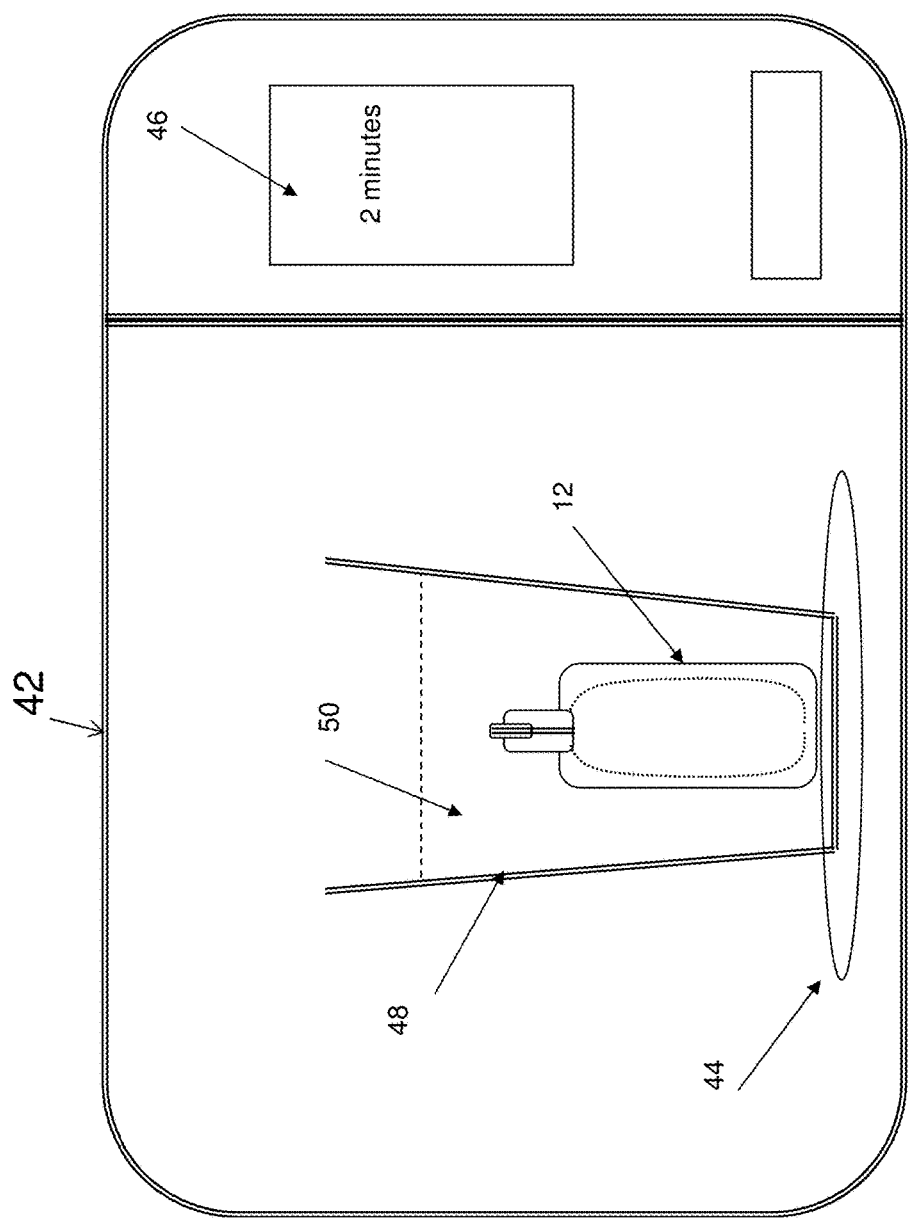
FIG. 3B is a block diagram that illustrates features of the present invention of another method of heating the oil in the sachet for middle ear infection cure.

Alternatively as illustrated in FIG. 3B, if the sachet 12 is made of metal foil, the sachet 12 can also be heated in a glass 48 with about 8 OZ of water 50 inside the microwave oven 42.

Based on these instructions, the sachet is put in a microwave oven just before use for only notionally 30 seconds, as set by a timer 46, to heat the oil in the sachet up to in the range of 110 to 115 Fahrenheit degrees. It is believed that such a limited use of microwave oven would heat the oil for this purpose. Notionally ten to twenty degrees of temperature over the body temperature of 98.4 Fahrenheit degrees provides for warm oil and not hot oil. This degree of warmness of oil provides for a therapeutic effect when the warn oil drops enter the ear canal.

Temperature of the sachet and the oil may be higher when first heated in the microwave oven than this notionally 110 to 115 Fahrenheit degrees. The temperature of the oil would drop when the sachet is removed from the microwave oven and before it is used.

The head of a person with middle ear infection is positioned on a side to have one ear facing up before dropping the oil in the ear canal and the head is stayed in position for substantially a few minutes to have the oil flow in to the middle ear.

Up to five drops of heated oil is squeezed into an ear canal of a person with severe ear itching indicative of a middle ear infection. Fewer drops, such as one to three may be used for children. The ear is plugged with the cotton plug 18 and head is turned on the other side for dropping the oil into the other ear.

An apparatus for natural cure for middle ear infection has a single use sachet. The sachet has a pouch and the pouch holds a limited quantity of mustard essential oil. The sachet has a neck and a dropper and sachet can be squeezed to flow drops of the oil for dropping into an ear canal. The single use sachet is packaged in a packaging with two absorbent ear plugs.

The oil is warmed up to in the range of 110 to 115 Fahrenheit degrees to provide a therapeutic effect as the oil is dropped in the ear canal. The head is positioned on a side to have one ear facing up before dropping the oil in the ear canal and the head is stayed in position for substantially a few minutes to have the oil flow in to the middle ear. The ear is plugged with the cotton plug and head is turned on the other side for dropping the oil into the second ear.

The sachet is put in a microwave oven just before use for substantially 15 seconds to heat the oil to be warm. Up to five drops of heated oil from the sachet is squeezed into an ear canal of a person with severe ear itching indicative of a middle ear infection.

An apparatus for natural cure for middle ear infection has a single use sachet. The sachet has a pouch and the pouch holds a limited quantity of mustard essential oil. The sachet has a neck and a dropper and sachet can be squeezed to flow drops for dropping the oil into an ear canal. The oil, while in the sachet, is heated to a therapeutic temperature before being used.

The sachet has attached to it a liquid crystal thermometer strip for indicating the temperature of the oil. The thermometer is used to gauge the temperature of oil as being below 115 Fahrenheit degrees before use in the ear canal when the sachet and the oil have been heated to a therapeutic temperature.

The sachet is put in a microwave oven just before use for substantially 30 seconds to warm the oil and up to five drops of heated oil is squeezed into an ear canal of a person with severe ear itching indicative of a middle ear infection. The oil is warmed up to be in the range of 110 to 115 Fahrenheit degrees to provide a therapeutic effect as the oil is dropped in the ear canal.

Figure 4:
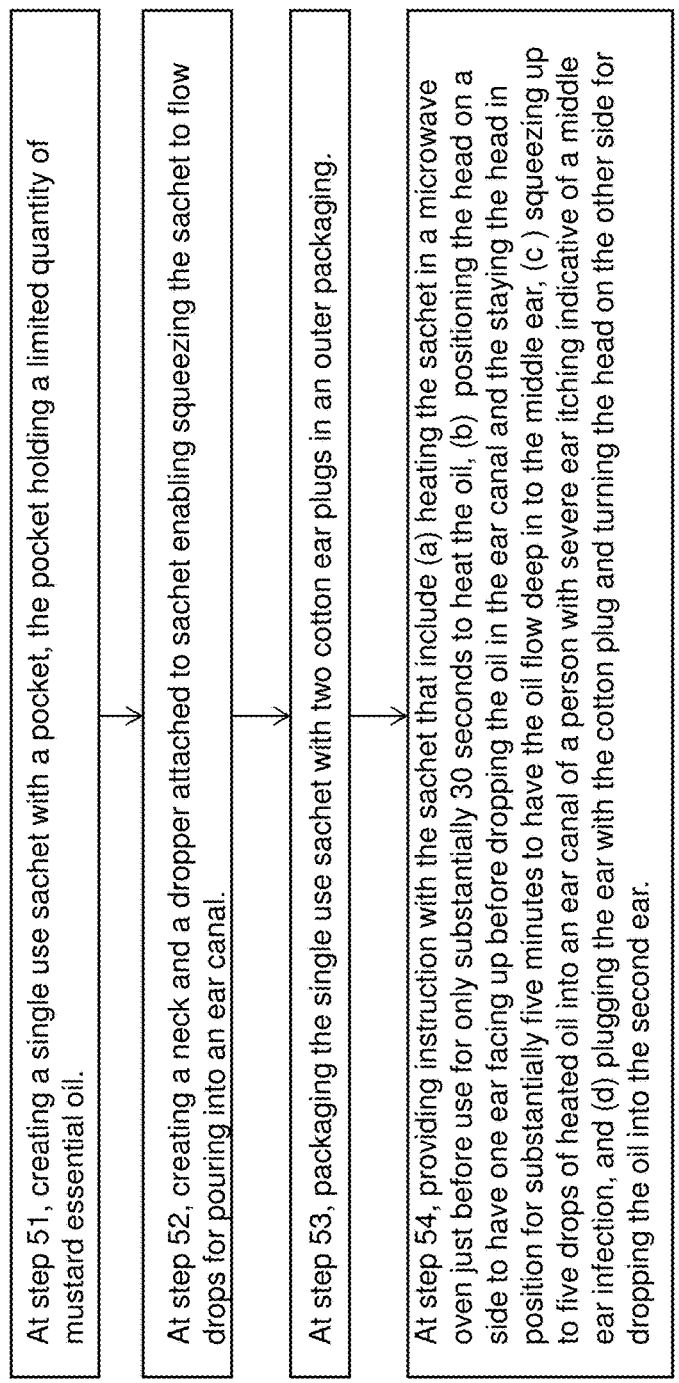
FIG. 4 is a method diagram that illustrates features of the present invention of a cure for middle ear infection.

A method is illustrated with reference to FIG. 4, where not all the steps may be used or used in the order specified.

At step 51, creating a single use sachet with a pocket, the pocket holds a limited quantity of mustard essential oil.

At step 52, creating a neck and a dropper attached to sachet enabling squeezing the sachet to flow drops for pouring into an ear canal.

At step 53, packaging a single use sachet 12, in an outer packaging, along with two cotton ear plugs.

At step 54, providing instruction with the sachet that include (a) heating the sachet in a microwave oven just before use for only substantially 30 seconds to heat the oil, (b) positioning the head on a side to have one ear facing up before dropping the oil in the ear canal and the staying the head in position for substantially five minutes to have the oil flow deep in to the middle ear, (c) squeezing up to five drops of heated oil into an ear canal of a person with severe ear itching indicative of a middle ear infection, and (d) plugging the ear with the cotton plug and turning the head on the other side for dropping the oil into the other ear.

This method of treatment of middle ear infection, it is believed, usually provides an instant relief from the itching and usually cures the infection in a single treatment as above.

While the particular invention, as illustrated herein and disclosed in detail is fully capable of obtaining the objective and providing the advantages herein before stated, it is to be understood that it is merely illustrative of the presently preferred embodiments of the invention and that no limitations are intended to the details of construction or design herein shown other than as described in the appended claims.

What is claimed is:

1. An apparatus for natural treatment for a middle ear infection, comprising:
    a single use sachet having a reservoir, a neck and a dropper, wherein the single use sachet has a channel that extends from the reservoir to the dropper at a distal end of the single use sachet, and wherein the single use sachet is, configured to be held vertically using a human hand over an ear canal, when a patient's head is positioned on a side to have one ear facing up;
    the single use sachet holds a liquid consisting of mustard essential oil, and the single use sachet is configured for delivering a plurality of drops of the mustard essential oil in the ear canal for treating the middle ear infection in the patient.

2. The apparatus as in claim 1, further comprising:
    the single use sachet is packaged in a package with at least two absorbent ear plugs.

3. The apparatus as in claim 1, further comprising:
    the single use sachet is configured to be heated to warm up the oil to a temperature substantially in the range of 110 to 115 Fahrenheit degrees to provide a therapeutic effect as the oil is dropped in the ear canal.

4. The apparatus as in claim 1, further comprising:
    a cotton plug to be used by inserting into the ear canal after delivering the oil into the ear canal using the single use sachet, and the patient's head is stayed in position on the side for substantially a few minutes to have the oil flow in to the middle ear.

5. The apparatus as in claim 4, further comprising:
    the cotton plug is configured to plug the ear to prevent the oil from flowing out of the ear canal when the patient's head is turned on the other side for dropping the oil into the other ear.

6. The apparatus as in claim 1, further comprising:
    a. wherein the single use sachet is configured to be put in a microwave oven just before delivering the oil to the ear canal, for substantially 15 seconds to heat the oil to be warm; and
    b. wherein, the single use sachet is configured to be squeezed to deliver up to five drops of heated oil from the single use sachet into the ear canal with severe ear itching indicative of the middle ear infection.

7. A method for a natural treatment for a middle ear infection, comprising the steps of:
    providing a single use sachet, wherein the single use sachet has a reservoir, a neck and a dropper, wherein the single use sachet has a channel that extends from the reservoir to the dropper at a distal end of the single use sachet and, wherein the single use sachet is configured to be held vertically using a human hand over an ear canal of a patient's head, wherein the single use sachet holds a liquid consisting of mustard essential oil;
    positioning the patient's head on a side to have one ear facing up;
    using the single use sachet to drop a plurality of drops of the mustard essential oil in the ear canal for treating the middle ear infection in the patient.

8. The method as in claim 7, further comprising the steps of:
    a. heating the single use sachet in a microwave oven just before the step of using the single use sachet, for substantially 15 seconds to warm the oil; and
    b. wherein the step of using comprises squeezing up to five drops of warm oil into the ear canal of the patient with severe ear itching that is indicative of the middle ear infection.

9. The method as in claim 8, wherein the step of heating the single use sachet further comprising:
    warming the oil up to in the range of 110 to 115 Fahrenheit degrees to provide a therapeutic effect as the oil is dropped in the ear canal.

10. The method as in claim 7, further comprising the step of:
    packaging the single use sachet in a package that has at least two cotton ear plugs.

11. The method as in claim 7:
    wherein, the step of positioning the patient's head on the side to have one ear facing up occurs before dropping the oil in the ear canal; and
    further comprising the step of staying the patient's head in position for substantially a few minutes to have the oil flow deep in to the middle ear.

12. The method as in claim 11, further comprising the step of:
    plugging the ear with a cotton plug for preventing the oil from flowing out of the ear canal when turning the head on the other side for dropping the oil into the other ear.

13. An apparatus for natural treatment for a middle ear infection, comprising:
    a single use sachet, wherein the single use sachet holds a liquid consisting of mustard essential oil for treating a middle ear infection and wherein the single use sachet is configured to be heated to a therapeutic temperature before being used;
    the single use sachet has a reservoir, a neck and a dropper, wherein the single use sachet has a channel that extends from the reservoir to the dropper at a distal end of the single use sachet and the single use sachet is configured to be held vertically over an ear canal when a patient's head is positioned on a side to have one ear facing up, for the single use sachet to be squeezed to flow drops of the oil into the ear canal to treat the middle ear infection.

14. The apparatus as in claim 13, further comprising:
the single use sachet has attached to it a liquid crystal thermometer strip for indicating the temperature of the oil before squeezing the single use sachet to deliver the oil in the ear canal after the sachet and the oil have been heated to the therapeutic temperature.

15. The apparatus as in claim 13, further comprising:
the single use sachet is configured to be put in a microwave oven just before squeezing the sachet to warm the oil and wherein the single use sachet is configured to be squeezed to drop up to five drops of warmed oil into the ear canal with severe ear itching indicative of the middle ear infection.

16. The apparatus as in claim 13, further comprising:
wherein the oil is heated up to be in the range of 110 to 115 Fahrenheit degrees to provide a therapeutic effect as the warm oil is dropped in the ear canal.

\* \* \* \* \*